US008658710B2

(12) United States Patent
McKellop et al.

(10) Patent No.: US 8,658,710 B2
(45) Date of Patent: *Feb. 25, 2014

(54) OXIDATION-RESISTANT AND WEAR-RESISTANT POLYETHYLENES FOR HUMAN JOINT REPLACEMENTS AND METHODS FOR MAKING THEM

(75) Inventors: Harry A. McKellop, Los Angeles, CA (US); Fu-Wen Shen, Walnut, CA (US)

(73) Assignee: Orthopaedic Hospital, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/805,867

(22) Filed: May 24, 2007

(65) Prior Publication Data

US 2007/0293647 A1 Dec. 20, 2007

Related U.S. Application Data

(63) Continuation of application No. 10/258,762, filed as application No. PCT/US01/13839 on Apr. 27, 2001.

(60) Provisional application No. 60/200,525, filed on Apr. 27, 2000.

(51) Int. Cl.
*A61K 31/355* (2006.01)
*C08J 3/28* (2006.01)

(52) U.S. Cl.
USPC ............... 522/161; 623/23.58; 623/23.59; 264/494

(58) Field of Classification Search
USPC ............. 264/494; 522/161; 623/23.58, 23.59, 623/523.59
See application file for complete search history.

(56) References Cited

U.S. PATENT DOCUMENTS

| | | | |
|---|---|---|---|
| 5,414,049 A | 5/1995 | Sun et al. | |
| 5,449,745 A | 9/1995 | Sun et al. | |
| 5,466,530 A | 11/1995 | England et al. | |
| 5,505,984 A | 4/1996 | England et al. | |
| 5,543,471 A | 8/1996 | Sun et al. | |
| 5,577,368 A | 11/1996 | Hamilton et al. | |
| 5,650,485 A | 7/1997 | Sun et al. | |
| 5,721,334 A | 2/1998 | Burstein et al. | |
| 5,728,748 A | 3/1998 | Sun et al. | |
| 5,753,182 A | 5/1998 | Higgins | |
| 5,824,411 A | 10/1998 | Shalaby et al. | |
| 5,827,904 A | 10/1998 | Hahn | |
| 5,879,400 A | 3/1999 | Merrill et al. | |
| 6,017,975 A | 1/2000 | Saum et al. | |
| 6,143,232 A | 11/2000 | Rohr | |
| 6,165,220 A | 12/2000 | McKellop et al. | |
| 6,174,934 B1 | 1/2001 | Sun et al. | |
| 6,184,265 B1 | 2/2001 | Hamilton et al. | |
| 6,228,900 B1 | 5/2001 | Shen et al. | |
| 6,242,507 B1 | 6/2001 | Saum et al. | |
| 6,245,276 B1 | 6/2001 | McNulty | |
| 6,277,390 B1 | 8/2001 | Schaffner et al. | |
| 6,281,264 B1 | 8/2001 | Salovey et al. | |
| 6,316,158 B1 | 11/2001 | Saum et al. | |
| 6,355,215 B1 | 3/2002 | Poggie et al. | |
| 6,372,814 B1 | 4/2002 | Sun et al. | |
| 6,448,315 B1 | 9/2002 | Lidgren et al. | |
| 6,464,926 B1 | 10/2002 | Merrill et al. | |
| 6,468,258 B1 | 10/2002 | Shang | |
| 6,494,917 B1 | 12/2002 | McKellop et al. | |
| 6,503,439 B1 | 1/2003 | Burstein | |
| 6,562,540 B2 | 5/2003 | Saum et al. | |
| 6,641,617 B1 | 11/2003 | Merrill et al. | |
| 6,664,308 B2 | 12/2003 | Sun et al. | |
| 6,692,679 B1 | 2/2004 | McNulty et al. | |
| 6,800,670 B2 | 10/2004 | Shen et al. | |
| 6,818,020 B2 | 11/2004 | Sun et al. | |
| 2001/0027345 A1 | 10/2001 | Merrill et al. | |
| 2002/0007219 A1 | 1/2002 | Merrill et al. | |
| 2004/0156879 A1 | 8/2004 | Muratoglu et al. | |

FOREIGN PATENT DOCUMENTS

| | | |
|---|---|---|
| AU | 716762 | 1/1996 |
| AU | 727279 | 4/2000 |
| AU | 742681 | 5/2002 |
| EP | 0 722 973 A1 | 7/1996 |
| EP | 0 737 481 A1 | 10/1996 |
| EP | 0 995 450 B1 | 4/2000 |
| IT | 1284325 | 5/1998 |
| JP | A04-502028 | 4/1992 |
| JP | A 11-239611 | 7/1999 |
| JP | 3323728 | 6/2002 |
| WO | WO/90/06139 | 6/1990 |
| WO | WO 97/29793 | 8/1997 |
| WO | WO 98/01085 | 1/1998 |
| WO | WO 98/14223 | 4/1998 |
| WO | WO 98/16258 | 4/1998 |
| WO | WO 99/52474 | 10/1999 |
| WO | WO 01/80778 A1 | 11/2001 |

OTHER PUBLICATIONS

Aug. 2, 2001 International Search Report of PCT Application No. PCT/US01/13839.
May 15, 2002 Written Report of PCT Application No. PCT/US01/13839.
Aug. 19, 2002 Notification of Transmittal of International Preliminary Examination Report enclosing International Preliminary Examination Report of PCT Application No. PCT/US01/13839.
Jun. 10, 2003 Communication from the European Patent Office enclosing May 26, 2003 Supplementary European Search Report for European patent application No. 01934941.4.
Jul. 30, 2004 "Communication pursuant to Article 96(2) EPC" from the European Patent Office for European patent application No. 01934941.4.
Jun. 17, 2005 "Communication pursuant to Article 96(2) EPC" from the European Patent Office for European patent application No. 01934941.4.

(Continued)

*Primary Examiner* — Sanza McClendon
(74) *Attorney, Agent, or Firm* — McDermott Will & Emery LLP (57) ABSTRACT

The present invention presents methods for making oxidation-resistant and wear-resistant polyethylenes and medical implants made therefrom. Preferably, the implants are components of prosthetic joints, e.g., a bearing component of an artificial hip or knee joint. The resulting oxidation-resistant and wear-resistant polyethylenes and implants are also disclosed.

16 Claims, 1 Drawing Sheet

(56) References Cited

OTHER PUBLICATIONS

Jun. 29, 2006 "Communication pursuant to Article 96(2) EPC" from the European Patent Office for European patent application No. 01934941.4.
Nov. 25, 2004 Examiner's First Report from the Australian Intellectual Property Office for Australian patent application No. 2001261083.
Jan. 6, 2006 Examiner's Report No. 2 from the Australian Intellectual Property Office for Australian patent application No. 2001261083.
Mar. 3, 2006 Notice of Acceptance from the Australian Intellectual Property Office for Australian patent application No. 2001261083.
May 29, 2007 Japanese Patent Office's "Notice of Reasons for Rejections" of Japanese patent application No. 2001-577881.
Aug. 29, 2007 Official Communication from the European Patent Office regarding European patent application No. 01 934 941.4-2107.
Oral, E., et al., "Characterization of irradiated blends of α-tocopherol and UHMWPE," *Biomaterials*, 26: 6657-6663 (2005).
Muratoglu, O. K., et al., "Surface Crosslinking of UHMWPE Using Irradiation in Molten Sate for Total Joint Arthroplasty," 47$^{th}$ Ann. Meeting, Orthopaedic Research Society, Feb. 25-28, 2001, San Francisco, California, p. 1030.
Andreucetti, N. A., et al., "Effect of the Phenolic Antioxidants on the Structure of Gamma-Irradiated Model Polyethylene," *Radiat. Phys. Chem.*, 52 (1-6): 177-182 (1998).
Jaworska, E., et al., "Irradiation of Polyethylene in the Presence of Antioxidants," *Radiat. Phys. Chem.*,37 (2): 285-290 (1991).
Laermer, S. F., et al., "Alpha-Tocopherol (Vitamin E)—the Natural Antioxidant for Polyolefins," *J. Plastic Film & Sheeting*, 8: 228-248 (1992).
Laermer, S. F., et al., "Use of Biological Antioxidants as Polypropylene Stabilizers," *Plastics & Rubber Processing & Applications*, 14 (4): 235-239 (1990).
European Patent No. EP 1 276 436 B1, Dec. 31, 2008.
Oct. 13, 2009 "Communication of a Notice of Opposition" from the European Patent Office, enclosing the Sep. 29, 2009 Notice of Opposition to European Patent No. 1 276 436 B1, by DMV Marketing & Vertriebs GmbH.
Ruger et al., "Effects of Antioxidant on the Tribological Properties of Gamma Sterilized Ultra High Molecular Weight Polyethylene," 5$^{th}$ World Biomaterials Congress, May 29 to Jun. 2, 1996, Toronto, Canada, p. 522.
Pilcher et al., "The Effects of Sterilization on the Properties of Ultrahigh Molecular Weight Polyethylene (UHMWPE)," J. Southern Orthopaedic Assoc., vol. 3, No. 1, pp. 27-33 (Spring, 1994).
P. Sjovall, et al., "Vitamin E reduces free radical concentration in UHMWPE after gamma radiation," 6$^{th}$ World Biomaterials Congress Trans, Soc. Biomaterials, May 15-20, 2000, Hawaii, USA, vol. III, p. 1483.
Certificate of Patent for Japanese Patent No. 4256096, Feb. 6, 2009.
Claims of Japanese Patent No. 4256096, Feb. 6, 2009.
Jan. 9, 2009 Certified Determination of Allowance from the Japanese Patent Office for Japanese patent application No. 2001-577881.
Sep. 25, 2008 Interview Record of Japanese patent application No. 2001-577881.
Jun. 10, 2008 Final Rejection from the Japanese Patent Office for Japanese patent application No. 2001-577881.
Mar. 16, 2009 Communication from the European Patent Office enclosing the extended European search report for European patent application No. 08022565.9.
Nov. 11, 2009 "Communication pursuant to Article 94(3) EPC" from the European Patent Office for European patent application No. 08022565.9.
Minutes from Jan. 27, 2011, Oral Proceedings in EP 01 934 941.4 Patent Opposition.
Feb. 24, 2011 Decision of Opposition Division in EP 01 934 941.4 Patent Opposition.
Oonishi, et al., "Wear of high-dose gamma irradiated polyethylene in total joint replacement—long term radiological evaluation" in Trans 44$^{th}$ Ann Mtg., Orthopaedic Res. Soc. 23: 97-17 (1998).

Facts on UHMWPE: Part One of a Series on Ultra-High Molecular Weight Polyethylene, "Overview and Fundamentals of UHMWPE" (Howmedica, Inc., 1994).
Communication Pursuant to Article 94(3) EPC (Examination Report) for European Application No. 08022565.9, dated May 10, 2013, entitled "Oxidation-resistant and wear-resistant polyethylenes for human joint replacements and methods for making them."
Schmalzried, et al., "Rationale for crosslinked polyethylene in hip and knee replacement surgery," Current Opinion in Orthopaedics, 11: 397-402 (2000).
Decision of the Boards of Appeal of the European Patent Office, dated Mar. 25, 2013, for Appeal No. T1029/11-3.2.08, European Patent Application 01934941.4, entitled "Oxidation-resistant and wear-resistant polyethylenes for human joint replacements and methods for making them."
Communication Pursuant to Article 101(1) and Rule 31(2) to (3) EPC, dated Apr. 12, 2013, re further examination of the opposition for European Patent Application 01934941.4, entitled "Oxidation-resistant and wear-resistant polyethylenes for human joint replacements and methods for making them."
Rimnac, C.M., et al., "Post-Irradiation Aging of Ultra-High Molecular Weight Polyethylene", *J. Bone & Joint Surgery*, 76-A(7):1052-1056 (1994).
Walsh, H., et al., "Factors that Determine the Oxidation Resistance of Molded 1900: Is it the Resin or the Molding", Poster Session—Polyethylene, 46th Annual Meeting, Orthopaedic Res. Soc., Mar. 12-15, 2000, Orlando, Florida, U.S.A., p. 543.
Mori, A., et al., "Mechanical Behavior of UHMWPE When Mixed with Vitamin E", Nakashima Medical Division, Nakashima Propeller Co., Ltd., hand-out at the 47th Ann. Mtg., Orthopaedic Res. Soc., Feb. 25-28, 2001, San Francisco, California.
Mori et al., "Effects of Manufacturing Method and Condition on UHMWPE Wear", Soc. Biomaterials, Sixth World Biomaterials Congress Transactions, p. 1122, year 2000.
Walsh, H. A., et al., "A True, Reproducible Accelerated Aging Protocol to Mimic 5 Year Shelf Aging of UHMWPE", Poster Session—Polyethylene, 46th Ann. Mtg., Orthopaedic Res. Soc., Mar. 12-15, 2000, Orlando, Florida, U.S.A., p. 542.
Mori et al., "Mechanical Behavior of UHMWPE When Mixed with Vitamin E", Poster Session—Polyethylene, 47th Ann. Mtg., Orthopaedic Res. Soc., Feb. 25-28, 2001, San Francisco, California, p. 1017.
Tomita, N., et al., "Prevention of Fatigue Cracks in Ultrahigh Molecular Weight Polyethylene Joint Components by the Addition of Vitamin E", *J. Biomed Mater Res (Appl Biomater)* 48: 474-478 (1999).
Kurtz, S. M., et al., "Advances in the processing, sterilization, and crosslinking of ultra-high molecular weight polyethylene for total joint arthroplasty", *Biomaterials* 20: 1659-1688 (1999).
McKellop, H., et al., Development of an Extremely Wear-Resistant Ultra High Molecular Weight Polyethylene for Total Hip Replacements, *J. Ortho. Res.* 17 (2): 157-167 (1999).
McKellop, H. A., et al., "Bearing Surfaces in Total Hip Replacements: State of the Art and Future Developments", *AAOS Instructional Course Lectures*, 50: 165-179 (2001).
Sanford, W.M. et al., "Accelerated oxidative aging testing of UHMWPE", Trans. 41st Ann. Mtg. Orthopaedic Res. Soc., p. 119-20 (1995).
Sun. D.C., et al., "A simple accelerated aging method for simulations of long-term oxidative effects in UHMWPE implants", 42nd Ann. Mtg., Orthopaedic Res. Soc., p. 493 (1996).
Shen, F-W., et al., "Potential Errors in FTIR Measurement of Oxidation in Ultrahigh Molecular Weight Polyethylene Implants", *J. Biomed Mater Res (Appl Biomater)* 48 : 203-210 (1999).
DesJardins, J. D., et al., "The use of a force-control led dynamic knee simulator to quantify the mechanical performance of total knee replacement designs during functional activity" *J. Biomechanics* 33: 1231-1242 (2000).
Shen et al., "Irradiation of Chemically Crosslinked Ultrahigh Molecular Weight Polyethylene", *J. Polym. Sci., Part B: Polym. Phys.*, 34:1063-1077 (1996).
Shen, F-W., PhD. Dissertation:"Effect of Irradiation on Chemically Crosslinked Ultrahigh Molecular Weight Polyethylene" UMI Company, Ann Arbor, Michigan (1995).

OXIDATION-RESISTANT AND WEAR-RESISTANT POLYETHYLENES FOR HUMAN JOINT REPLACEMENTS AND METHODS FOR MAKING THEM

This patent application is a continuation of co-pending U.S. patent application Ser. No. 10/258,762, filed on Oct. 25, 2002, which in turn is the national phase filing of Patent Cooperation Treaty application number PCT/US01/13839, filed on Apr. 27, 2001, entitled "Oxidation-Resistant and Wear-Resistant Polyethylenes for Human Joint Replacements and Methods for Making Them", which in turn is a continuation-in-part of U.S. provisional patent application Ser. No. 60/200,525, filed on Apr. 27, 2000, entitled "Oxidation-Resistant and Wear-Resistant Polyethylene for Human Joint Replacements". The entire contents of the predecessor applications are hereby expressly incorporated by reference.

TECHNICAL FIELD OF THE INVENTION

The present invention relates to polyethylenes. It discloses methods for enhancing the wear resistance of polyethylenes without inducing oxidative degradation, by crosslinking oxidation-resistant polyethylenes. The polyethylenes disclosed herein are useful for making articles such as medical implants, for example, components of artificial joints such as acetabular cups.

BACKGROUND OF THE INVENTION

Ultrahigh molecular weight polyethylene (hereinafter referred to as "UHMWPE") is commonly used to make prosthetic joints such as artificial hip joints. A conventional way of making implants is to machine them out of extruded UHMWPE or block molded UHMWPE. Alternatively, the implants are directly molded from UHMWPE. The implants are then packaged and next sterilized with radiation, gas plasma, or ethylene oxide. The sterilized packaged implants are then sold and the implants are removed from their packages when the surgeons are ready to place them in the patients' bodies.

In recent years, it has become increasingly apparent that wear of acetabular cups of UHMWPE in artificial hip joints introduces many microscopic wear particles into the surrounding tissues. The reaction to these particles includes inflammation and deterioration of the tissues, particularly the bone to which the prosthesis is anchored. Eventually, the prosthesis becomes painfully loose and must be replaced.

Improving the wear resistance of the UHMWPE socket and, thereby, reducing the rate of production of wear debris would extend the useful life of artificial joints and permit them to be used successfully in younger patients. Consequently, numerous modifications in physical properties of UHMWPE have been proposed to improve its wear resistance.

UHMWPE components are also known to undergo a spontaneous, post-fabrication increase in crystallinity and changes in other physical properties. {See e.g., Rimnac, C. M., et al., *J. Bone & Joint Surgery*, 76-A(7):1052-1056 (1994)}. These changes occur even in stored (non-implanted) prostheses after sterilization with gamma radiation ("gamma radiation sterilization") which is typically used for sterilization irradiation. The industrial standard for the gamma sterilization dose is between 2.5 Mrad to 4 Mrad. Typically, 3 to 3.5 Mrad is used.

Gamma radiation initiates an ongoing process of chain scission, crosslinking, and oxidation or peroxidation involving the free radicals formed by the irradiation. These degradative changes may be accelerated by oxidative attack from the joint fluid bathing the implant. Oxidation due to post-irradiation aging of UHMWPE has been associated with pitting, delamination and fracture in total hip replacements. (Walsh, H., et al., "Factors that Determine the Oxidation Resistance of Molded 1900: Is it the Resin or the Molding", Poster Session-Polyethylene, 46th Annual Meeting, Orthopaedic Res. Soc., Mar. 12-15, 2000, Orlando, Fla., U.S.A., page 543, first sentence. Hereinafter referred to as "Walsh p. 543, supra"). Additionally, many studies have shown that oxidation due to open-air gamma-irradiation sterilization of UHMWPE components is associated with delamination and fracture in artificial knee-joints. {Mori, A., et al., "Mechanical Behavior of UHMWPE When Mixed with Vitamin E", Nakashima Medical Division, Nakashima Propeller Co., Ltd., hand-out at the 47th Ann. Mtg., Orthopaedic Res. Soc., Feb. 25-28, 2001, San Francisco, Calif., first sentence. Hereinafter referred to as "Mori Hand-Out".} In another publication, Mori et al., indicate that: "Apparently, it is widely recognized through numerous research projects that the largest cause of wear on [UHMWPE], used as the bearing surface in artificial joints, is the oxidative degradation following γ-ray irradiated sterilization in air." (Mori et al., "Effects of Manufacturing Method and Condition on UHMWPE Wear", Society for Biomaterials, Sixth World Biomaterials Congress Transactions, p 1122, year 2000, first sentence. Hereinafter referred to as "Mori p. 1122, supra").

Consequently, several companies have modified the method of gamma radiation sterilization to improve the oxidation-resistance and thus the wear resistance of the UHMWPE components. For example, in the case of UHMWPE acetabular cups, this has typically involved packaging the cups either in an inert gas (e.g., Stryker-Osteonics-Howmedica, Inc., Rutherford, N.J., USA), in a partial vacuum (e.g., Johnson & Johnson, Inc., New Brunswick, N.J., USA) or with an oxygen scavenger (e.g., Sulzer, Inc., Winterthur, Switzerland) during gamma radiation sterilization. Alternatively, gas plasma or ethylene oxide are used to sterilize the implant in order to avoid the free radicals generated by irradiation sterilization.

Further, in recent years, there have been reports that some UHMWPE may be particularly resistant to oxidation. Starting from the 1970's, Zimmer Inc. (Warsaw, Ind., USA) has been making an UHMWPE commonly known in the industry as "net-shaped molded UHMWPE" (also known as "direct-molded UHMWPE").

Walsh, H., et al., reported that "components made by directly molding 1900 resin are resistant to post irradiation aging for periods up to 10 years. Further, these directly molded devices have excellent clinical track records and exhibit extremely low incidences of pitting, delamination and fracture", and that "components made by direct molding of 1900 resin have a unique resistance to oxidation. Machined components from extruded 1900 bar or compression molded 1900 sheet do not exhibit the same oxidation resistance. It is also clear from Table 1 that extruded bar and compression molded sheet of 4150 resin are also susceptible to post irradiation aging . . . Table 2 shows that directly molding either 4150 or 1990 resin provides an oxidation-resistant material. As the resin used in the directly molded 4150 was the same lot as that used in the extruded bars, the only difference between the samples was the manufacturing method." (Left col., first and second sentences, and right col., second and third paragraphs of Walsh p. 543, supra).

Since the rate of oxidation is slow, and typically takes 5 years of post-irradiation aging (i.e., 5 years of shelf aging) for density values to rise above 0.95 g/cc, an indicator of oxidation, Walsh et al reported an accelerated aging protocol to mimic 5 years shelf aging of UHMWPE. (Walsh, H. A., et al., "A True, Reproducible Accelerated Aging Protocol To Mimic 5 Year Shelf Aging of UHMWPE", Poster Session-Polyethylene, 46th Ann. Mtg., Orthopaedic Res. Soc., Mar. 12-15, 2000, Orlando, Fla., U.S.A., page 542. Hereinafter referred to as "Walsh p. 542, supra").

Walsh p. 542, supra, reported that specimens directly molded from 4150HP powder to provide a modulus of 600-800 MPa did not oxidize, when aged with its accelerated aging protocols, as compared to HSS/PolyHi Solidur/Ticona reference extruded 4150HP, which was machined into specimens.

On the other hand, Mori p. 1122, supra, compared specimens: (1) machined from GUR 4150HP ram extruded bar stock; (2) custom molded directly from GUR1150 resin and using compression pressure of 45 kgf/cm$^2$; and (3) custom molded directly from GUR1150 resin and using compression pressure of 200 kgf/cm$^2$. Mori et al., observed that directly compression molded specimens with 45 kgf/cm$^2$ compression pressure and ram extruded specimens showed highly-developed oxidation compared to the 200 kgf/cm$^2$ directly compression molded specimen. Thus, Mori et al., reported that: "It is generally said that direct compression molded UHMWPE provide an unexpected resistance to oxidation. However, the results obtained from this study reveal that granted directly compression molding method was used, unsuitable conditions of the process could cause less resistance to oxidation." (Mori p. 1122, supra, first paragraph under the "Discussion" section).

In another paper, Mori, A., et al., compared two groups of UHMWPE specimens made from: (1) directly molded from UHMWPE powder (GUR1020, Ticona) at 10 MPa, and (2) directly molded from a mixture of GUR1020 powder and Vitamin E, also at 10 MPa. Mori et al., then gamma sterilized in air (at 25 kGy which is equivalent to 2.5 Mrad) and then applied accelerated aging techniques to both groups. Mori et al reported that the addition of Vitamin E to UHMWPE powder provided a unique resistance to oxidation, and preserved the initial mechanical properties. (Mori et al., "Mechanical Behavior of UHMWPE When Mixed with Vitamin E", Poster Session-Polyethylene, 47th Ann. Mtg., Orthopaedic Res. Soc., Feb. 25-28, 2001, San Francisco, Calif., p. 1017. Hereinafter referred to as "Mori p. 1017, supra"). N. Tomita, a co-author of Mori p. 1017, supra, has previously reported that his gamma-irradiated vitamin-E-containing specimens demonstrated no subsurface crack formation and no flaking-like destruction. {Tomita, N., et al., "Prevention of Fatigue Cracks in Ultrahigh Molecular Weight Polyethylene Joint Components by the Addition of Vitamin E", *J. Biomed Mater Res (Appl Biomater)* 48: 474-478 (1999)}.

Mori et al teach that: "Recently the practice of crosslinking UHMWPE after gamma-ray or electron-beam irradiation has developed to improve resistance to oxidation. However, the process of crosslinking of UHMWPE is complex, and it is difficult to remove the free radicals created by irradiation. It is suggested that the addition of harmless Vitamin E is a very simple and extremely effective method to prevent oxidation degradation and maintain the stability of UHMWPE component in artificial joints." (Mori 1017, supra, paragraph bridging left and right columns. See also, Mori hand-out, second and third last sentences).

SUMMARY OF THE INVENTION

The present invention presents methods for making and selecting for oxidation-resistant and wear-resistant polyethylenes and medical implants made therefrom. Preferably, the implants are components of prosthetic joints, e.g., a bearing component of an artificial hip, knee, or other joint. The resulting oxidation-resistant and wear-resistant polyethylenes and implants are also disclosed.

DETAILED DESCRIPTION OF THE INVENTION

The invention described herein draws on previously published work and patent applications. By way of example, such work consists of scientific papers, abstracts, posters, hand-outs, and patents. All of these publications and patent applications, cited previously or below, are hereby incorporated by reference to the same extent as if each independent publication or patent application was specifically and individually indicated to be incorporated by reference.

I. Choices of Polyethylenes

Abbreviations used in this application are as follows:
PE—polyethylene
UHMW—ultra-high molecular weight
UHMWPE—ultra-high molecular weight polyethylene
HMW—high molecular weight
HMWPE—high molecular weight polyethylene The present invention relates to polyethylenes in general, and preferably HMWPE and UHMWPE. For ease of discussion, the following discussion uses HMWPE and UHMWPE as examples of a polyethylene and is not intended to limit the invention to merely HMWPE and UHMWPE. This invention also presents finished articles (i.e., end products) made of polyethylenes. Non-limiting examples of these finished articles are medical implants. Again, for ease of discussion, the following discussion uses an acetabular cup as a non-limiting example of a medical implant and is not intended to limit the invention to merely an acetabular cup.

The preferred polyethylenes are HMW polyethylene (HMWPE) and UHMW polyethylene (UHMWPE). HMWPE have molecular weights ranging from about $10^5$ grams per mole to just below $10^6$. UHMWPE have molecular weights equal to or higher than $10^6$ grams per mole, preferably from $10^6$ to about $10^7$. The polyethylenes are generally between about 400,000 grams per mole to about 10,000,000.

For implants, the preferred polyethylenes are those that are wear resistant and have exceptional resistance to chemical degradation. UHMWPE is the most preferred polyethylene as it is known for these properties and is currently widely used to make acetabular cups for total hip prostheses and components of other joint replacements. Examples of UHMWPE are those having molecular weight ranging from about 1 to $8 \times 10^6$ grams per mole, examples of which are: GUR 4150 or 4050 (Hoechst-Celanese Corporation, now known as Ticona, League City, Tex.) with a weight average molecular weight of 5 to $6 \times 10^6$ grams per mole; GUR 4130 with a weight average molecular weight of 3 to $4 \times 10^6$; GUR 4120 or 4020 with a weight average molecular weight of 3 to $4 \times 10^6$; RCH 1000 (Hoechst-Celanese Corp.) with a weight average of molecular weight of $4 \times 10^6$ and HiFax 1900 of 2 to $4 \times 10^6$ (HiMont, Elkton, Md.).

Ticona is the world's largest producer of medical grade UHMWPE. Historically, companies which make implants have used polyethylenes such as HIFAX 1900, GUR 4020, GUR 4120 and GUR 4150 for making acetabular cups.

UHMWPE is commercially available in two forms, one with and the other without calcium stearate. Examples of UHMWPE with calcium stearate are GUR 4120, 4130, 4150 and RCH 1000. Examples of UHMWPE without calcium stearate are GUR 1050 (also known as GUR 4050), 1020 (also known as GUR 4020), and HiFax 1900. Both forms of UHMWPE are within the definition of "UHMWPE" as used in this patent application. For the nomenclature and discussion of the different UHMWPE, their nomenclature and manufacturers, See Kurtz, S. M., et al., "Advances in the processing, sterilization, and crosslinking of ultra-high molecular weight polyethylene for total joint arthroplasty", Biomaterials 20: 1659-1688 (1999)(hereinafter referred to as "Kurtz, et al., supra").

Polyethylenes can generally be obtained in any ground, morselized, or pelleted form that can be molded or extruded into a larger solid piece. In this form, the polyethylenes are usually available as "polyethylene powder", "polyethylene flake" and "polyethylene resin" which are synonymous terms. For ease of discussion, the following discussion will use the term "polyethylene powder". Thus, one skilled in the art would realize that, if he wishes, he could replace the "polyethylene powder" discussed in this application (including its claims) with any ground, morselized, or pelleted form of polyethylene.

"Net shaped molding" and "direct molding" are synonymous terms used in the art; so are "net-shaped molded" and "direct-molded". For ease of discussion, this application will use the term "direct molding" and "direct-molded". Some commercially available polyethylene implants are produced by direct molding; that is, by placing the original polyethylene powder into a mold and applying sufficient heat and pressure to fuse the powder into the final shape of the implant or almost the final shape of the implant such that only minimal finish-machining is needed to make the implant.

In contrast, instead of direct molding, the majority of UHMWPE components used in artificial joints over the past three decades were either machined from ram-extruded bar stock, or were machined from molded blocks. Thus, the term "preformed polyethylene", such as "preformed UHMWPE", is used herein to mean UHMWPE which are used as the starting materials from which implants are machined. Such preformed UHMWPE are consolidated by ram extrusion (also known as "ram extruded UHMWPE"); and compression molding which is also known as block molding of UHMWPE powder into bar, rods, sheets, blocks, slabs or the like ("block molded UHMWPE"). Thus, non-limiting examples of such preformed UHMWPE are: extruded UHMWPE bar, compression molded UHMWPE block and sheets.

The term "reference preformed UHMWPE" means conventional UHMWPE extruded bars and conventional UHMWPE compression molded block.

The term "oxidation-resistant" as applied to polyethylenes (which include HMWPE and UHMWPE, as in "oxidation-resistant polyethylene", "oxidation-resistant HMWPE", and "oxidation-resistant UHMWPE") means a polyethylene that is more resistant to oxidation, for example, as caused by the free radicals that are induced during irradiation with a gamma source or an electron beam, than reference preformed UHMWPE. The implant made from oxidation-resistant UHMWPE is also referred to as an "oxidation-resistant implant".

Applicants' review of the current art show that the developers of oxidation-resistant polyethylenes (discussed in "Background of the Invention", above) have advocated their use in artificial joints primarily on the grounds that their resistance to oxidation results in less degradation of their mechanical properties and/or wear resistance when they are gamma irradiation sterilized in the range of 2.5 to 4 Mrads that is standard in the industry. However, applicants realize that this method of manufacture does not improve the wear resistance over that of typical gamma-sterilized implants of the past, which is unacceptably high in many patients, particularly the younger, more active patients who subject their joints to a high number of wear cycles per year. Some advocates of oxidation-resistant UHMWPE have criticized the use of elevated levels of radiation crosslinking to improve wear resistance. For example, Mori et al stated that: "Recently the practice of crosslinking UHMWPE after gamma-ray or electron-beam irradiation has developed to improve resistance to oxidation. However, the process of crosslinking of UHMWPE is complex, and it is difficult to remove the free radicals created by irradiation. It is suggested that the addition of harmless Vitamin E is a very simple and extremely effective method to prevent oxidation degradation and maintain the stability of UHMWPE component in artificial joints." (Mori 1017, supra, paragraph bridging left and right columns. See also, Mori hand-out, second and third last sentences).

On the other hand, crosslinking of a polyethylene is known to improve the wear resistance in industrial implants. Applicants tested the following: (1) chemically crosslinked acetabular cups produced by mixing a peroxide with UHMWPE powder and then molding the cups directly to shape; (2) gamma radiation-crosslinked acetabular cups produced by exposing conventional extruded UHMWPE bar stock to gamma radiation at various doses from 3.3 to 100 Mrad, remelting the bars to extinguish residual free radicals (i.e., to minimize long-term oxidation), and then machining the cups by conventional techniques. In hip-joint simulator tests lasting as long as 5 million cycles, both types of crosslinked cups exhibited dramatically improved resistance to wear. McKellop, H., et al., "Development of An Extremely Wear-Resistant Ultra High Molecular Weight Polyethylene for Total Hip Replacements, *J. Ortho. Res. Soc.* 17: 157-167(1999). For a review of conventional and industrial methods by which gamma or electron beam are used to irradiate conventional extruded UHMWPE bar stock to increase its crosslinking and thus wear resistance, and then remelt or anneal the bar stock to extinguish residual free radicals (i.e., to minimize long-term oxidation), and subsequently machining implants from the bar stock, and various studies using implant simulator, see, e.g., H. A. McKellop, "Bearing Surfaces in Total Hip Replacements: State of the Art and Future Developments", *AAOS Instructional Course Lectures,* 50: 165-179 (2001); and Kurtz et al., supra; and McKellop, H., et al., "Development of An Extremely Wear-Resistant Ultra High Molecular Weight Polyethylene for Total Hip Replacements, *J. Ortho. Res. Soc.* 17: 157-167(1999).

In the present invention, applicants recognize that, if one begins with an oxidation-resistant polyethylene and increases its wear resistance by increasing its level of crosslinking above that generated by the dose of radiation typically used to conventionally sterilize an implant (that is, above the range of 2.5 to 4 Mrads), then it is possible to produce an implant that has the desired high resistance to oxidation in combination with an improved wear resistance, making the implant particularly suitable for use in younger and more active patients than has been advisable in the past. Thus the present invention provides for a wear-resistant and oxidation-resistant implant by fabricating the implant from an oxidation-resistant polyethylene, including either shaping (such as machining) it from a preformed polyethylene, or by direct molding; packaging said implant, preferably in a low-oxygen atmosphere, and subjecting the packaged implant to a radiation dose above the range used for conventional sterilization in order to increase the level of crosslinking and, thereby, improve the wear resistance above that obtained with conventional radiation sterilization. Thus, the present invention provides for a way to produce oxidation-resistant implants, orthopaedic materials comprising polyethylenes, and polyethylenes that are more wear resistant than the conventional polyethylenes disclosed in the conventional arts, such as those described by the authors Mori et al., Tomita et al., and Walsh et al., supra.

The method of the present invention is also easier and cheaper to carry out than the conventional methods:

In the present invention, since the polyethylene has been formed in a manner that renders it highly resistant to oxidation, despite the presence of free radicals, there is no need to thermally treat the polyethylene during or after radiation crosslinking (e.g., by annealing or remelting) in order to extinguish the residual free radicals, and thus simplifying the manufacturing process. In addition, in the present invention, it is possible to use direct molded polyethylene components such as implants, which is not possible if remelting or annealing of the UHMWPE are required, since this may cause excessive distortion of an implant. In addition, since the oxidation-resistant polyethylene remains oxidation-resistant despite the presence of free radicals, the present invention also has the advantage of allowing for the use of gamma or electron beam to sterilize the component, rather than gas plasma or ethylene oxide that are currently used to avoid the free radicals generated by irradiation sterilization. The ability to use irradiation sterilization is an added advantage since gas plasma or ethylene oxide may not be appropriate for some modular types of implants because of the low penetration of gas plasma or ethylene oxide into the interfaces between the components of the implant.

Another advantage of the invention is that the irradiation crosslinking of the finished implant to improve its wear resistance and the irradiation sterilization may be done simultaneously in a single step. Thus, the methods of the present invention are simpler and more cost-efficient than the conventional methods.

The following describes the invention in more detail:

III. Oxidation-Resistant Polyethylenes

A. Method A

Applicants note that there are publications claiming that direct molding of UHMWPE produces a finished article of greater resistance to oxidation than a finished article machined from an extruded bar or molded block. The improvement is due to a more uniform pressure and temperature applied to the finished article during direct molding.

This method is exemplified by the commercially available oxidation-resistant direct molded implant (commercially available from Zimmer, Inc., discussed in the "Background of the Invention", above).

However, Mori p. 1122 has noted that direct molded (using 45 kgf/cm$^2$ pressure) specimens were less oxidation resistant than specimens machined from conventional ram extruded bar stock. On the other hand, direct molded (using 200 kgf/cm$^2$ pressure) specimens were more oxidation resistant than specimens machined from conventional ram extruded bar stock. Thus, Mori et al., reported that: "It is generally said that direct compression molded UHMWPE provide an unexpected resistance to oxidation. However, the results obtained from this study reveal that granted directly compression molding method was used, unsuitable conditions of the process could cause less resistance to oxidation." (Mori p. 1122, supra, under the "Discussion" section).

In view of the concern expressed above in Mori p. 1122, for the present invention, Method A preferably has the added modification(s) of Method B, below, in order to provide the suitable conditions for producing oxidation-resistant implants. Applicants also note that due to the concern of Mori p. 1122, one skilled in the art should apply the routine testing procedures described in the section "Testing and Selection Procedures", below, to ensure that he obtains his desired oxidation-resistant and wear-resistant polyethylene and implant.

2. Method B

This Method B has four aspects to it, each of which represents a modification. In Method B, each of the aspects can be applied alone, or in combination with one or more of the other aspects, to polyethylene processed by extrusion, by block molding, or by direct molding in order to make an oxidation-resistant polyethylene or implant. Thus, Method B could be applied to Method A and/or Method C.

Method B: Aspect 1

Applicants realize that adding one or more antioxidants (for economical and efficiency sake, one anitoxidant is preferred), such as those known in the chemical, polymer, and biological arts, would render the polyethylene oxidation resistant. Non-limiting examples of conventional antioxidants which may be used are vitamin A, vitamin C and vitamin E; and common antioxidants used to prevent or inhibit the oxidation of polymer, such as, members of the classes of phenols, aromatic amines, and salts and condensation products of amines and aminophenols with aldehydes, ketones, and thio compounds. Non-limiting examples of the members of the foregoing classes are paraphenylene diamines and diarylamines.

An example of the application of this aspect is found in Mori et al and Tomita et al who used Vitamin E to improve the oxidation resistance of their UHMWPE. (Mori Hand-Out, Mori p. 1122, Mori p. 1017, and Tomita et al., J. Biomed Mater Res, supra.)

Method B: Aspect 2

This aspect seeks to reduce or remove the amount of oxygen present in the polyethylene after it is fused (whether by extrusion, block molding, or direct molding, into, e.g., a solid bar, block, rod sheet or direct molded implant) in order to reduce the amount of oxidation that occurs during irradiation and thereafter. This can be done, for example, by placing the powder in a suitable container and causing an inert gas to flow through the powder in order to flush out the air (which contains oxygen) that is mixed with the powder. In addition, whether or not the powder has been flushed with inert gas, the container can be pressurized with an inert gas and maintained under pressure in order to force the inert gas into the powder, thereby displacing the air (which contains oxygen) from the powder. In addition, whether or not the powder has been flushed and/or pressurized with inert gas, the container can be evacuated and maintained under vacuum in order to draw out oxygen that is mixed with the powder and/or absorbed into the powder. In addition, whether or not one or more of the previous steps have been taken, the fusing of the powder (whether by extrusion, block molding or direct molding) can be done in a low oxygen atmosphere, such as an atmosphere of inert gas, to minimize mixing of air (which contains oxygen) with the polyethylene during the fusing process. These procedures are not generally exclusive and are additive and will reduce oxygen present in the polyethylene after it is fused such that the polyethylene implant will be more resistant to oxidation during irradiation, and during storage prior to use, and during use in vivo. Alternatively, the resulting polyethylene or implant may be stored with an oxygen absorbent or in any one of conventional low-oxygen conditions, instead of storing in vacuum or inert gas.

An example of the application of this aspect is found in Sun et al., U.S. Pat. No. 5,414,049, supra which discloses: "A medical implant made of polymeric material having an increased oxidation resistance is formed by a method including the steps of placing a resin powder in a sealed container. A substantial portion of the oxygen is removed from the sealed container by either a vacuum, an oxygen absorbent or by flushing with inert gas. The container is then repressurized with a gas such as nitrogen, argon, helium or neon so that long term storage may be possible. On use, the resin is transferred to a forming device which both melts and forms the resin in an oxygen reduced atmosphere to produce a polymeric raw material such as a rod or bar stock. The medical implant is then formed from this raw material annealed and sealed in an airtight package in an oxygen reduced atmosphere." (In the "Abstract" section of Sun et al., U.S. Pat. No. 5,414,049).

Method B: Aspect 3

This aspect fuses the polyethylene powder at a higher pressure, a higher temperature, and/or for a longer period of time than is conventionally used in order to achieve better fusion of the polyethylene powder, since it has been shown that diffusion of oxygen into the polyethylene occurs preferentially along the boundaries between the poorly or incompletely fused polyethylene powder or flakes. See, e.g., Mori p. 1122, supra. In this aspect of Method B, the pressure is preferably about 10 MPa or higher, and more preferably about 14 MPa or higher; the temperature is preferably about 175° C. or higher, and more preferably about 200° C. or higher; the time is preferably about 30 minutes or longer, and more preferably about 1 hour or longer.

An example of the application of this aspect is found in Mori p. 1122, supra, which showed that specimens custom molded directly from GUR1150 resin under elevated compression pressure of 200 kgf/cm$^2$ had improved oxidation index compared to those produced under compression pressure of 45 kgf/cm$^2$. Applicants note that 45 kgf/cm$^2$ (about 4.4 MPa) is at the low end of the range for conventional molding pressure, and more importantly, 200 kgf/cm$^2$ (about 19.6 MPa) is higher than the conventional molding pressure.

The use of elevated temperature, elevated pressure, and a longer period for fusing the polyethylene is also found in England et al's U.S. Pat. Nos. 5,466,530 and 5,505,984, discussed in further detail in Method C, below.

Method B: Aspect 4

When a polyethylene is irradiated, the irradiation generates free radicals. The free radicals that are present in the amorphous regions immediately crosslink or oxidize. Thus, if the irradiation is conducted in low oxygen atmosphere, the free radicals in the amorphous regions would tend to immediately crosslink instead of oxidize due to the lack of oxygen. The free radicals that have not crosslinked or oxidized after irradiation are primarily trapped in the crystalline regions of the polyethylene. Over time, these residual free radicals migrate to the amorphous regions. If the implant is removed from a low oxygen atmosphere after irradiation, these residual radicals can encounter oxygen molecules that have diffused into the amorphous regions, and oxidation can occur. Therefore, if there is a lower percentage of crystalline polyethylene, then there will be proportionately fewer free radicals and, therefore, less long-term oxidation.

Thus, the present aspect of Method B seeks to reduce the percentage of crystalline polyethylene which in turn reduces the residual free radicals in the polyethylene after irradiation, and which in turn reduces long-term oxidation. A non-limiting way to reduce the crystallinity of a polyethylene is to quench (i.e., rapidly cool) a polyethylene after it has been heated and fused, which results in a lower crystallinity in the quenched polyethylene.

An example of the application of this aspect is found in Example 1, below, wherein the molten UHMWPE specimen that had been molded at 170° C. and a ram pressure of 7.5 MPa for two hours was removed from the press and very rapidly cooled ("quenched") in a liquid nitrogen pool.

Another example of the application of this aspect is found in Walsh p. 543, supra, which reported its directly molded UHMWPE samples were more oxidation resistant than samples machined from extruded bar or compression molded sheet. The direct molding of the UHMWPE samples was conducted at 8.1 MPa, 165° C. and a cooling rate of greater than 175° C. per minute ("quenching"). Walsh p. 542, supra, also reported that specimens directly molded from 4150HP UHMWPE powder to provide a modulus of 600-800 MPa, was oxidation resistant.

Burstein and Li, U.S. Pat. No. 5,721,334, "Process for Producing Ultra-High Molecular Weight Low Modulus Polyethylene Shaped Articles Via Controlled Pressure and Temperature and Compositions and Articles Produced Therefrom", was issued Feb. 24, 1998. The patent's co-inventor (Stephen Li) also co-authored Walsh p. 542 and 543, supra. This patent noted that the shaped UHMWPE articles made from its method are useful as the bearing surface of total knee joints, prosthetic hip joint cups, and as other prosthetic shapes for replacement of other joints of the human body. Significantly, the patent does not disclose that its methods produce oxidation-resistant UHMWPE. However, the patent discloses a five-step direct molding method which contains a quenching step 5. The method is described as follows: "1. Filling a mold with powdered UHMWPE; 2. Covering the mold with a piston; 3. Raising the temperature of the mold . . . while simultaneously applying a pressure . . . to the mold and its contents; 4. Maintaining the pressure and temperature . . . ; 5. Dropping the temperature of the molded part, either completely or in part at a rate between about 4.degree. and about 175 degree.C./minute, either while maintaining the mold at the molding pressure, at pressure less than the molding pressure, or under no external applied pressure. Dropping the temperature of the molded part may be accomplished either by cooling the part directly by contact with a suitable cooling fluid such as water or air or by cooling the mold." (U.S. Pat. No. 5,721,334, supra, "Summary of the Invention", second para.). Applicants note that the quenching rate in step 5 of the patent (of about 175 degree.C./minute) overlaps that of Walsh p. 543, supra (greater than 175° C. per minute); and the modulus of the patented UHMWPE shaped article (elastic modulus of about 500 Mpa to about 800 Mpa) overlaps that of Walsh p. 542, supra (modulus of 600-800 Mpa). In view of the foregoing, applicants believe that the patent's method could be used to produce oxidation-resistant UHMWPE implants. The details and preferred ranges for the parameters for carrying out the method are found in the patent to enable one skilled in the art to produce the UHMWPE implants. One skilled in the art could apply the routine testing procedures described in the section "Testing and Selection Procedures", below, to test the UHMWPE implants produced under the patented method to determine whether they are oxidation-resistant.

3. Method C

Applicants also recognize that if polyethylene powder is molded into a smaller size than the conventional size of UHWMPE blocks, the small molded polyethylene will have improved oxidation resistance due to a more uniform pressure and temperature applied to the finished article during direct molding. The small molded polyethylene is preferably about 4-inch in diameter or smaller, and more preferably from about 0.5-inch to about 4-inch in diameter.

An example of the application of Method C is found in England, et. al.'s U.S. Pat. Nos. 5,466,530, "Biocompatible Components Fabricated from A Substantially Consolidated Stock of Material" (issued Nov. 14, 1995) and 5,505,984, "Method for Forming Biocompatible Components Using An Isostatic Press" (issued Apr. 9, 1996). Even though the patentees do not recognize that their methods for producing wear-resistant UHMWPE biocompatible component also produce oxidation-resistant component, applicants believe that their methods can produce oxidation-resistant components. Thus, the patents' method can be applied to produce implants and the implants can be tested according to the method disclosed in the section "Testing And Selection Procedures", below, to select for the oxidation-resistant implants. Applicants' belief is based on the fact that: (1) the patents' method meets the criteria of Method C, herein, in that their molded UHMWPE were in smaller sizes, e.g., of 1.5-inch diameter to 4-inch diameter, than the conventional size of UHWMPE molded blocks; and (2) their method (during its hot isostatic step) uses the elevated pressure, temperature and a longer period for fusing the UHMWPE than are favored in applicants' Method B, Aspect 3, above.

The England et al's method includes enclosing UHMWPE powder in a first container and subjecting the first container to a cold isostatic pressure treatment which forms an incompletely consolidated stock from the powder. The incompletely consolidated stock is removed from the first container and is placed in a second container which is then located within a hot isostatic press and is subjected to a hot isostatic pressure treatment. The hot isostatic pressure treatment forms the relatively completely consolidated stock from the incompletely consolidated stock. The relatively completely consolidated stock is then machined into an implant. With regard to the size of the consolidated stock, the patent states that: "For example, smaller diameters of the completely consolidated stock (e.g., 1½ inches) typically require less time to become fully compacted, while larger diameters of completely consolidated stock, such as 4 inches, typically require more time to become fully cured." (U.S. Pat. No. 5,466,530, under "Detailed Description of the Preferred Embodiment", paragraph 26). The hot isostatic press operates from about 365.degree.F. to about 420.degree.F. When the hot isostatic press reaches approximately 365.degree.F., the pressure is also increased over a 1 to 2 hour period to a pressure preferably between about 7,500 to about 10,000 psi (i.e., between about 52 to about 69 MPa). Further details of the method and the preferred ranges of parameters are to be found in the patents.

IV. Irradiation Steps

The oxidation-resistant polyethylene implant may be irradiated using conventional methods known in the art, but modified to apply the radiation dose disclosed in the present invention. Non-limiting examples of conventional irradiation methods are found in the references cited in this application. For a review of industrial and conventional irradiation methods as applied to polyethylene implants, see also, H. A. McKellop, *AAOS Instructional Course Lectures*, 50: 165-179 (2001), supra; and Kurtz et al., supra.

In order to minimize oxidation of the surface layer of the implant during and after irradiation, the implant is preferably packaged in a low-oxygen atmosphere, for example, under a vacuum; in an inert gas such as nitrogen, helium, or argon; or with an oxygen scavenger. Known methods for such low-oxygen atmosphere packaging may be used, such as those used by the companies as described in "Background of the Invention", above.

The irradiation for crosslinking and irradiation for sterilization steps may be performed separately (whether one precedes the other). However, for efficiency sake, preferably the packaged implant is exposed to a radiation source which simultaneously sterilizes and crosslinks the implant to improve its wear resistance. Conventional radiation may be used, non-limiting examples of which are gamma radiation and electron beam radiation. The preferred radiation is by gamma radiation. As discussed above, conventional irradiation methods may be used, but modified to apply the radiation dose disclosed in the present invention. It has been reported that comparable amounts of crosslinking of a polyethylenes, induced by gamma radiation or electron beam radiation, produced comparably low wear rates (For a review of the reports, see, e.g., H. A. McKellop, "Bearing Surfaces in Total Hip Replacements: State of the Art and Future Developments", *AAOS Instructional Course Lectures*, 50: 165-179 (2001); and Kurtz et al., supra).

Since the wear resistance of a polyethylene is known to be improved with increasing levels of radiation-induced crosslinking, the radiation dose may be higher than the range of 2.5 to 4 Mrads that is typically used simply to sterilize a polyethylene component.

The irradiation dose is preferably from about 5 to about 100 Mrad. In the case of UHMWPE, the radiation dose is more preferably from about 5 to about 25 Mrad, and most preferably from about 5 to about 10 Mrad. This most preferable range is based on achieving a reasonable balance between improved wear resistance and minimal degradation of other important physical properties. These ranges may be used as starting ranges for other polyethylenes, as discussed further in the section "V. TESTING AND SELECTION PROCEDURES", below.

On the other hand, if a user is primarily concerned with reducing wear, and other physical properties are of secondary concern, then a higher dose than the above stipulated most preferable range (e.g., 5 to 10 Mrad) may be appropriate. If the user is concerned with the physical properties and balancing them with wear resistance, he may modify the radiation dose according to the further teaching below. The optimum radiation dose is preferably based on the dose received at the level of the bearing surface in the final product.

Instead of using the above range of radiation dose as a criterion, the appropriate amount of crosslinking may be determined based on the degree of swelling, gel content, or molecular weight between crosslinks after irradiation. This alternative is based on the applicant's findings in WO 98/01085, "Crosslinking of Polyethylene for Low Wear Using Radiation and Thermal Treatments", of the Orthopaedic Hospital et al., published Jan. 15, 1998, and McKellop, H., et al., *J. Ortho. Res. Soc.* 17: 157-167(1999), supra, that acetabular cups made from UHMWPE falling within a preferred range of these physical parameters have reduced or non-detectable wear. The ranges of these physical parameters preferably include one or more of the following: a degree of swelling of between about 1.7 to about 3.6; molecular weight between crosslinks of between about 400 to about 3,500 g/mol; and a gel content of between about 95% to about 99%. A preferred polyethylene or final product has one or more, and preferably all, of the above characteristics.

These parameters can also be used as starting points for applying the method (but absent the annealing or remelting of WO 98/01085, supra) described in the second aspect of the invention in WO 98/01085 for determining the desired radiation dose to balance the improvement in wear resistance with other desired physical or chemical properties, such as polyethylene strength or stiffness.

The above considerations are further discussed in the following section.

V. Testing and Selection Procedures

Applicants recognize that different users, such as manufacturers, of polyethylene implants may have different criteria regarding the acceptable combination of oxidation resistance, wear resistance, and other important mechanical properties (such as fatigue resistance), and these criteria may differ for different types of implants for a given user or manufacturer. Nevertheless, from the discussion herein, one skilled in the art applying the present invention will know how to use established techniques for measuring oxidation resistance, wear resistance and other mechanical properties to determine whether these meet his individual criteria.

That is, one skilled in the art may use the methods disclosed in the present invention to make a candidate polyethylene, or he may choose a member of the polyethylene class as a candidate, and apply the following routine tests to select for an improved oxidation resistance and wear resistance polyethylene and an implant made therefrom of the present invention which meet his desired characteristics.

The following presents a non-limiting example of the routine selection steps he may use. He may choose a member of the polyethylene class as a candidate ("unmodified polyethylene") or, if he wishes to modify the polyethylene ("modified polyethylene"), he may choose one or more of the steps described above (in Methods A, B, and C, discussed above) for increasing the oxidation resistance of the polyethylene. These steps are, for the most part, non-exclusive and additive in their ability to improve the oxidation resistance of polyethylene. The polyethylene (whether modified or unmodified, as he desires) may be routinely tested for its oxidation-resistance according to methods known in the art. For example, by irradiating the polyethylene to the desired level of crosslinking and then subjecting it to shelf aging, as described in Example 1, below, or to accelerated aging by exposure to elevated temperature in air (or, if desired, pressurized oxygen) for an extended period of time and then measuring the resultant level of oxidation. Suitable methods for accelerated aging are known in the art and are described in, for example, Sanford, W. M. et al., "Accelerated oxidative aging testing of UHMWPE", Trans. 41st Ann. Mtg. Orthopaedic Res. Soc., p. 119 (1995); Sun. D. C., et al., "A simple accelerated aging method for simulations of long-term oxidative effects in UHMWPE implants", 42nd Ann. Mtg., Orthopaedic Res. Soc., p. 493 (1996); and Walsh p. 542, supra.

The resultant amount of oxidation in the polyethylene may be measured, for example, by cutting the polyethylene specimen into segments and then measuring the level of oxidation at and below the surface using Fourier-transform infrared spectroscopy, as described, for example, by Shen, F. W. et al., "Potential Errors In FTIR Measurement of Oxidation in Ultrahigh Molecular Weight Polyethylene Implants", *J. Biomedical Materials Research, J. Applied Biomaterials,* 48 (93), 203-210 (1999) or by measuring the density as a function of depth into the sample, as described by Walsh p. 542 and 543, supra. This is advisable in view of the observation in Mori 1122, supra, that some directly molded polyethylene may not be oxidation-resistant.

As discussed above, the wear resistance of UHMWPE increases with increased crosslinking {see, e.g., McKellop, H., et al., *J. Ortho. Res. Soc.* 17: 157-167(1999), supra}. As discussed above, for the present invention, the amount of crosslinking radiation for UHMWPE may be from about 5 to about 100 Mrads, preferably from about 5 to about 25 Mrads, and most preferably from about 5 to about 10 Mrads. Thus, one skilled in the art may use these ranges as a starting point for his irradiation step for UHMWPE. The quantitative relationship between the level of crosslinking and the wear resistance may be different for polyethylenes other than UHMWPE, and can be determined by exposing the candidate polyethylene to a range of radiation doses, preferably between about 5 to about 100 Mrads, and performing suitable wear tests on each to develop a dose-wear relationship.

Conventional wear tests such as sand slurry, pin-on-disk, and implant simulator tests may be used to test the wear resistance of the polyethylene specimens. Preferably, implants are directly molded from the polyethylene or machined from it, and the wear resistance as a function of level of crosslinking may be determined by subjecting the implants to laboratory wear simulation in a suitable simulator for the particular implant to be tested. For example, the many known conventional simulators may be used. For example, the bearing surface of an implant for a hip joint, such as the medical acetabular cup implant may be tested in the hip simulators described in McKellop, H., et al., *J. Ortho. Res. Soc.* 17: 157-167 (1999), supra. Similarly, a knee simulator is described in Desjardins, J. B., et al., "The Use Of A Force-Control Dynamic Knee Simulator To Quantify The Mechanical Performance Of A Total Knee Replacement Design, During Functional Activity" *J. Biomechanic* 33(10): 1231-1242 (2000). For a review of wear and oxidation research involving simulators, see e.g., Kurtz et al., supra.

In addition, since crosslinking may reduce other mechanical properties, such as fracture toughness, dose-response relationships may be developed for these properties as well by subjecting specimens that have been crosslinked to various levels to appropriate established tests of the specific mechanical properties, which may be found, for example, in the published standards of the American Society for Testing and Materials (ASTM).

As noted above, the criteria for an optimum balance among oxidation resistance, wear resistance and other mechanical properties may vary among different users and manufacturers, and among types of implants, such as hip joints compared to knee joints, for a given manufacturer or user. Nevertheless, the optimum values of the preparation parameters for fabricating a polyethylene with adequate amounts of oxidation resistance, wear resistance and other mechanical properties may be routinely determined as described above, and the number of specimens and tests required may be minimized by the application of established design-of-experiments (DOE) statistical techniques.

Having described the invention, the following examples are presented to illustrate and support the invention, and are not to be construed as limiting the scope of the invention.

EXAMPLE 1

Oxidation of Gamma-Irradiated Ultra-High Molecular Weight Polyethylene

Method and Materials

Original powder of medical-grade UHMWPE, GUR 415 (Hoechst, Tex., USA), with a weight-average molecular weight of approximately $6\times10^6$, was used as received. Specimens were compression molded according to the following procedures. The original powder of UHMWPE was placed in a 1 mm thick circular mold (5 centimeter inside diameter) between two stainless steel plates that were covered with aluminum foil. The press was pre-heated to 170° C. and then the UHMWPE was compression molded for two hours at 170° C. and a ram pressure of 7.5 MPa applied on the mold and polyethylene. After two hours, the pressure was increased to 15 MPa and the specimen was slowly cooled in the press to room temperature.

Alternatively, for the quench-crystallized UHMWPE, the molten specimen that had been molded at 170° C. and a ram pressure of 7.5 MPa for two hours was removed from the press and very rapidly cooled ("quenched") in a liquid nitrogen pool. The specimens were gamma sterilized in air at room temperature to an average dose of about 3.4 Mrad.

The properties of UHMWPE were analyzed before and immediately after gamma sterilization. One set of gamma-sterilized specimens was stored on the shelf in ambient air for about 6.5 years.

Thermal properties of UHMWPE with or without gamma sterilization were analyzed using differential scanning calorimetry. Samples weighing about 6-9 mg were heated from 50° C. at 10° C./min in a differential scanning calorimeter (Perkin-Elmer DSC-4) to 170° C. The melting temperature was identified from the peak of the melting endotherm. Indium was used for calibration of the temperature and heat of fusion. The degree of crystallinity was calculated as the heat of fusion of UHMWPE sample divided by that of an ideal polyethylene crystal (292 J/g).

The degree of crosslinking of the irradiated UHMWPE was assessed from the swell ratios of the materials. A sheet, approximately 1 mm thick and weighing about 0.4 grams, was cut out of the irradiated specimens, and the sol-fraction was extracted by boiling in p-xylene for 72 hours, with 0.5 weight percent of antioxidant (2,6-di-t-butyl-4-methyl phenol) added to prevent oxidation. After extraction, the gel was transferred to fresh p-xylene and allowed to equilibrate at 120° C. for 2 hours. The swollen gel was then quickly transferred to a weighing bottle, covered, and weighed. The data was obtained as the average of five measurements. Samples were then soaked in acetone and dried at 60° C. in a vacuum oven to constant weight. The swell ratio was calculated as weight of swollen gel divided by that of dried extracted gel, and the gel content was determined from the ratio of the weight of the dried extracted to the initial nonextracted sample. The swell ratio was used to calculate the network chain density, number-average molecular weight between crosslinks and crosslink density, according to the theory of Flory and Rehner {Shen et al., *J. Polym. Sci., Polym. Phys.*, 34:1063-1077 (1996)}.

The oxidation of the shelf-aged gamma sterilized UHMWPE was assessed by Fourier transform infrared spectroscopy (FTIR). Segments of the shelf-aged UHMWPE were embedded in poly(methyl methacrylate) (PMMA) and microtomed into 200-micron thick slices. Oxidation measurements were taken using a transmission FTIR (Mattson Genesis II, Wisconsin, USA) mounted with a microscope (Spectra-Tech IR Plan, Spectra-Tech, Inc., Connecticut, USA). Measurements were taken using a 0.1×0.1 millimeter window, starting at the surface and moving across the thickness in 100-micron steps, using 64 scans summation at a resolution of 16 cm$^{-1}$. Oxidation was calculated as the height of the carbonyl absorption at 1717 cm$^{-1}$ divided by the height of the reference peak at 2022 cm$^{-1}$.

RESULT AND DISCUSSION

The thermal properties, swell ratio and gel content are shown in Table 1.

TABLE 1

| Type of UHMWPE | Peak Melting Point (° C.) | | Cystallinity (%) | | Swell Ratio | M.W. Between Crosslinks (g/mol) | Gel Content (%) |
|---|---|---|---|---|---|---|---|
| | Without Irrad. | With Irrad. | Without Irrad. | With Irrad. | With Irrad. | With Irrad. | With Irrad. |
| Slow-cooled | 132.6 | 135 | 49.2 | 55.8 | 8.4 | 21,753 | 70.8 |
| Quenched | 129.3 | 130 | 44.2 | 49.8 | 6.0 | 10,952 | 76.7 |

"Irrad." denotes irradiation
"M.W." denotes number-average molecular weight

Figure 1:
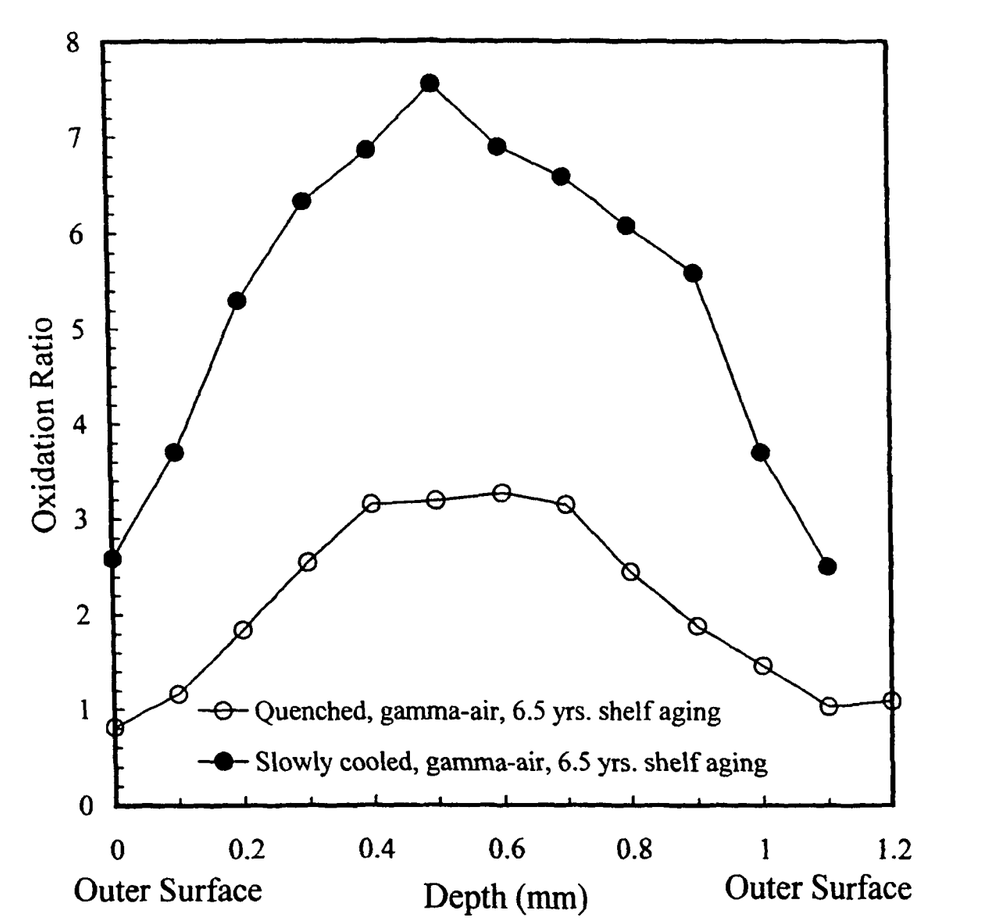
FIG. 1 graphically shows the oxidation profiles of slow-cooled and quenched crystallized UHMWPE that were gamma radiation sterilized in air at an average dose of 3.4 Mrad and subsequently stored in air at room temperature for about 6.5 years.

The oxidation profiles of the shelf-aged gamma sterilized UHMWPE are shown in FIG. 1. As shown in FIG. 1, the quenched UHMWPE exhibited an improved oxidation resistance, with a reduction of about 57% in the peak oxidation, as compared to the slow-cooled UHMWPE.

Although the foregoing invention has been described in some detail by way of illustration and example for purposes of clarity and understanding, it will be obvious that various modifications and changes which are within the skill of those skilled in the art are considered to fall within the scope of the appended claims. Future technological advancements which allow for obvious changes in the basic invention herein are also within the claims.

We claim:

1. A method for producing a wear-resistant and oxidation-resistant medical implant of a joint prosthesis, said method comprising the steps of:
   (I) providing an oxidation-resistant medical implant of a joint prosthesis comprising a polyethylene component; and
   (II) irradiating the oxidation-resistant medical implant at a radiation dose of above 5 Mrad to about 25 Mrad so as to crosslink the implant thereby improving its wear resistance, without thermally treating the implant to extinguish free radicals in the irradiated and crosslinked implant during or subsequent to irradiating the oxidation-resistant implant; wherein the oxidation-resistant implant contains an antioxidant rendering it resistant to oxidation caused by free radicals generated by the irradiation of step (II); and the irradiated oxidation-resistant implant possesses the characteristics of: a degree of swelling of between about 1.7 to about 3.6; a molecular weight between crosslinks of between about 400 to about 3,500 g/mol; and a gel content of between about 95% to about 99%.

2. The method of claim 1, wherein the radiation dose is from above 5 Mrad to about 10 Mrad.

3. The method of claim 1, wherein the polyethylene is selected from the group consisting of: ultra high molecular weight polyethylene and high molecular weight polyethylene.

4. The method of claim 1, wherein the anti-oxidant is selected from the group consisting of: vitamin A, vitamin C, vitamin E, phenols, aromatic amines, salts and condensation products of amines with aldehydes, ketones, or thio compounds, and salts and condensation products of aminophenols with aldehydes, ketones, or thio compounds.

5. The method of claim 4, wherein the anti-oxidant is vitamin E.

6. The method of claim 1, wherein the irradiation is performed with radiation selected from the group consisting of: gamma radiation and electron beam radiation.

7. The method of claim 1, wherein the irradiation also sterilizes the implant.

8. The method of claim 1, wherein the oxidation-resistant medical implant is produced according to the process selected from the group consisting of: (a) mixing the anti-oxidant and polyethylene powder and fusing the mixture to produce an oxidation-resistant preformed polyethylene and machining the oxidation-resistant medical implant from the oxidation-resistant preformed polyethylene; and (b) mixing the anti-oxidant and the polyethylene powder and fusing the mixture in a mold to produce a direct molded oxidation-resistant medical implant.

9. The method of claim 8, wherein the polyethylene is selected from the group consisting of: ultra high molecular weight polyethylene and high molecular weight polyethylene.

10. The method of claim 1, wherein the polyethylene is selected from the group consisting of: ultra high molecular weight polyethylene and high molecular weight polyethylene; and the irradiation is performed with radiation selected from the group consisting of: gamma radiation and electron beam radiation.

11. The method of claim 10, wherein the anti-oxidant is selected from the group consisting of: vitamin A, vitamin C, vitamin E, phenols, aromatic amines, salts and condensation products of amines with aldehydes, ketones, or thio compounds, and salts and condensation products of aminophenols with aldehydes, ketones, or thio compounds.

12. The method of claim 1, wherein providing an oxidation-resistant medical implant comprises:

either (a) mixing the anti-oxidant and polyethylene powder and fusing the mixture to produce an oxidation-resistant preformed polyethylene and machining the oxidation-resistant implant from the oxidation-resistant preformed polyethylene or (b) mixing the anti-oxidant and the polyethylene powder and fusing the mixture in a mold to produce a direct molded oxidation-resistant medical implant; and packaging the oxidation-resistant implant in a sealed package.

13. The method of claim 12, wherein the irradiating the oxidation-resistant medical implant is performed while the implant is packaged in the sealed package.

14. The method of claim 12, wherein once the oxidation-resistant medical implant is packaged in the sealed package, and the oxidation-resistant implant remains in the sealed package until the implant is to be implanted.

15. The method of claim 12, wherein packaging the oxidation-resistant medical implant comprises packaging the oxidation-resistant medical implant in an airtight package in an oxygen reduced atmosphere.

16. The method of claim 1, wherein oxidation-resistant medical implant is irradiated at a radiation dose of above 10 Mrad to about 25 Mrad.

* * * * *

UNITED STATES PATENT AND TRADEMARK OFFICE
CERTIFICATE OF CORRECTION

PATENT NO. : 8,658,710 B2  
APPLICATION NO. : 11/805867  
DATED : February 25, 2014  
INVENTOR(S) : Harry A. McKellop et al.

Page 1 of 1

It is certified that error appears in the above-identified patent and that said Letters Patent is hereby corrected as shown below:

On the Title Page

ON PAGE 2:

In Item (56) Reference Cited, Other Publications: amend "Jan. 9, 2009 Certified Determination of Allowance from the Japanese Patent Office for Japanese patent application No. 2001-577881" to read --"Jan. 9, 2009 Certified <u>Copy of</u> Determination of Allowance from the Japanese Patent Office for Japanese patent application No. 2001-577881".--

Signed and Sealed this  
Third Day of June, 2014

Michelle K. Lee  
*Deputy Director of the United States Patent and Trademark Office*